(12) United States Patent
Horrigan et al.

(10) Patent No.: US 7,881,806 B2
(45) Date of Patent: Feb. 1, 2011

(54) MEDICAL LEAD DELIVERY DEVICE

(75) Inventors: John B. Horrigan, Beverly, MA (US);
Ryan T. Bauer, Plymouth, MN (US);
Patrick Senarith, Minneapolis, MN (US);
H. Allan Steingisser, Melrose, MA (US);
Pedro A. Mersgotte, Vadnais Heights, MN (US);
John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 666 days.

(21) Appl. No.: 11/694,242

(22) Filed: Mar. 30, 2007

(65) Prior Publication Data
US 2008/0242964 A1 Oct. 2, 2008

Related U.S. Application Data

(63) Continuation-in-part of application No. 11/555,004, filed on Oct. 31, 2006, now abandoned.

(51) Int. Cl.
*A61N 1/05* (2006.01)
(52) U.S. Cl. .................. 607/119; 607/115; 607/116
(58) Field of Classification Search ............ 607/5–122; 604/2
See application file for complete search history.

(56) References Cited

U.S. PATENT DOCUMENTS

| | | | |
|---|---|---|---|
| 4,209,019 A | 6/1980 | Dutcher et al. | |
| 4,545,390 A | 10/1985 | Leary | |
| 4,624,266 A | 11/1986 | Kane | |
| 4,646,755 A | 3/1987 | Kane | |
| 4,763,647 A | 8/1988 | Gambale | |
| 4,813,434 A | 3/1989 | Buchbinder et al. | |
| 4,844,092 A | 7/1989 | Rydell et al. | |
| 5,003,990 A | 4/1991 | Osypka | |
| 5,056,516 A | 10/1991 | Spehr | |
| 5,159,861 A | 11/1992 | Anderson | |
| D333,182 S | 2/1993 | Yoshikawa | |
| 5,304,218 A | 4/1994 | Alferness | |
| 5,312,338 A | 5/1994 | Nelson et al. | |
| 5,325,746 A | 7/1994 | Anderson | |
| 5,325,868 A | 7/1994 | Kimmelstiel | |
| 5,363,861 A * | 11/1994 | Edwards et al. | 600/585 |
| 5,381,790 A | 1/1995 | Kenasaka | |
| 5,383,922 A * | 1/1995 | Zipes et al. | 607/122 |
| 5,443,078 A | 8/1995 | Uflacker | |
| 5,549,109 A | 8/1996 | Samson et al. | |
| 5,575,814 A | 11/1996 | Giele et al. | |
| 5,579,780 A | 12/1996 | Zadini et al. | |

(Continued)

FOREIGN PATENT DOCUMENTS

WO   WO 2008/055025 A1   5/2008

*Primary Examiner*—Carl H Layno
*Assistant Examiner*—Paula J Stice
(74) *Attorney, Agent, or Firm*—Reed A. Duthler

(57) ABSTRACT

The medical lead delivery device combines features of a guidewire and a stylet in order to more easily and quickly deliver a lead to or through the coronary vein of a patient's heart. The medical lead delivery device includes an elongated body, a controller, a first and second spring, and a sleeve. The elongated body includes a proximal end and a distal end. The controller is disposed at the proximal end and provides enhanced control of the distal tip of the elongated body.

26 Claims, 10 Drawing Sheets

U.S. PATENT DOCUMENTS

| | | | |
|---|---|---|---|
| 5,606,981 A * | 3/1997 | Tartacower et al. | 600/585 |
| 5,697,964 A * | 12/1997 | Gates | 607/122 |
| 5,755,765 A | 5/1998 | Hyde et al. | |
| 5,967,978 A | 10/1999 | Littmann et al. | |
| 6,059,484 A | 5/2000 | Greive | |
| 6,516,230 B2 * | 2/2003 | Williams et al. | 607/116 |
| 6,836,687 B2 | 12/2004 | Kelley et al. | |
| 6,893,393 B2 | 5/2005 | Carrillo | |
| 6,950,689 B1 | 9/2005 | Willis et al. | |
| 6,973,352 B1 | 12/2005 | Tsutsui et al. | |
| 7,013,182 B1 * | 3/2006 | Krishnan | 607/122 |
| 7,151,965 B2 | 12/2006 | Osypka | |
| 7,156,868 B1 | 1/2007 | Nashef et al. | |
| 7,162,309 B2 | 1/2007 | Laske et al. | |
| 7,201,724 B2 | 4/2007 | Jarl et al. | |
| 7,322,944 B2 * | 1/2008 | Osawa et al. | 600/585 |
| 7,369,901 B1 * | 5/2008 | Morgan et al. | 607/127 |
| 7,637,863 B2 | 12/2009 | Deal et al. | |
| 2002/0055764 A1 | 5/2002 | Malonek et al. | |
| 2003/0009095 A1 | 1/2003 | Skarda | |
| 2003/0074040 A1 * | 4/2003 | Florio et al. | 607/119 |
| 2003/0216800 A1 | 11/2003 | Ebert et al. | |
| 2003/0229386 A1 * | 12/2003 | Rosenman et al. | 607/116 |
| 2004/0068299 A1 | 4/2004 | Laske et al. | |
| 2005/0113862 A1 | 5/2005 | Besselink | |
| 2005/0196424 A1 | 9/2005 | Chappa | |
| 2005/0203604 A1 | 9/2005 | Brabec et al. | |
| 2005/0222554 A1 | 10/2005 | Wallace et al. | |
| 2005/0227398 A1 | 10/2005 | Anderson et al. | |
| 2006/0085039 A1 * | 4/2006 | Hastings et al. | 607/9 |
| 2006/0167535 A1 | 7/2006 | Johnson | |
| 2007/0021812 A1 | 1/2007 | Manning et al. | |
| 2007/0185415 A1 | 8/2007 | Ressemann | |
| 2007/0233215 A1 | 10/2007 | Sommer et al. | |
| 2008/0103571 A1 | 5/2008 | Bauer et al. | |
| 2008/0161898 A1 | 7/2008 | Bauer et al. | |
| 2008/0242964 A1 | 10/2008 | Horrigan et al. | |
| 2008/0243195 A1 | 10/2008 | Sommer et al. | |
| 2008/0243215 A1 | 10/2008 | Sommer et al. | |

* cited by examiner

Detail A
Proximal Joint

MEDICAL LEAD DELIVERY DEVICE

CROSS-REFERENCE TO RELATED APPLICATIONS

This application is a continuation-in-part of U.S. patent application Ser. No. 11/555,004, filed 31 Oct. 2006 now abandoned. Further, cross-reference is hereby made to the following commonly-assigned and related U.S. patent applications: U.S. patent application Ser. No. 11/694,182 entitled "MAPPING GUIDELET" to Sommer et al.; U.S. patent application Ser. No. 11/694,205 entitled "CONTROLLER FOR A MEDICAL LEAD DELIVERY DEVICE" to Sommer et al.; both filed concurrently herewith and incorporated herein by reference in their entirety.

TECHNICAL FIELD

The present invention relates to medical devices and, more particularly, to delivery of implantable medical device leads.

BACKGROUND

Most commercially available cardiac pacing and defibrillation leads are placed by means of a stylet which is inserted into a central lumen through the lead, and is used to assist in pushing the lead through the vascular system and guiding it to a desired location. A guidewire, possessing a smaller diameter than a stylet, may also be used to place a lead. Guidewires extend entirely through the lead and out its distal end. The approach of using a guidewire to place cardiac pacing leads and cardioversion leads is disclosed in U.S. Pat. No. 5,003,990 issued to Osypka, U.S. Pat. No. 5,755,765 issued to Hyde et al, U.S. Pat. No. 5,381,790 issued to Kenasaka and U.S. Pat. No. 5,304,218 issued to Alferness.

Lead placement into the left heart is difficult since the veins are very small. Consequently, a stylet is initially used to get the lead down to the right atrium and locate the left coronary vein returning from the left outer area of the heart. From that point, a stylet is considered too big to enter the small left ventricle veins. The guidewire is then used for final placement of the lead in the small left ventricle veins.

BRIEF DESCRIPTION OF DRAWINGS

Aspects and features of the present invention will be appreciated as the same becomes better understood by reference to the following detailed description of the embodiments of the invention when considered in connection with the accompanying drawings, wherein.

DETAILED DESCRIPTION

Figure 1:
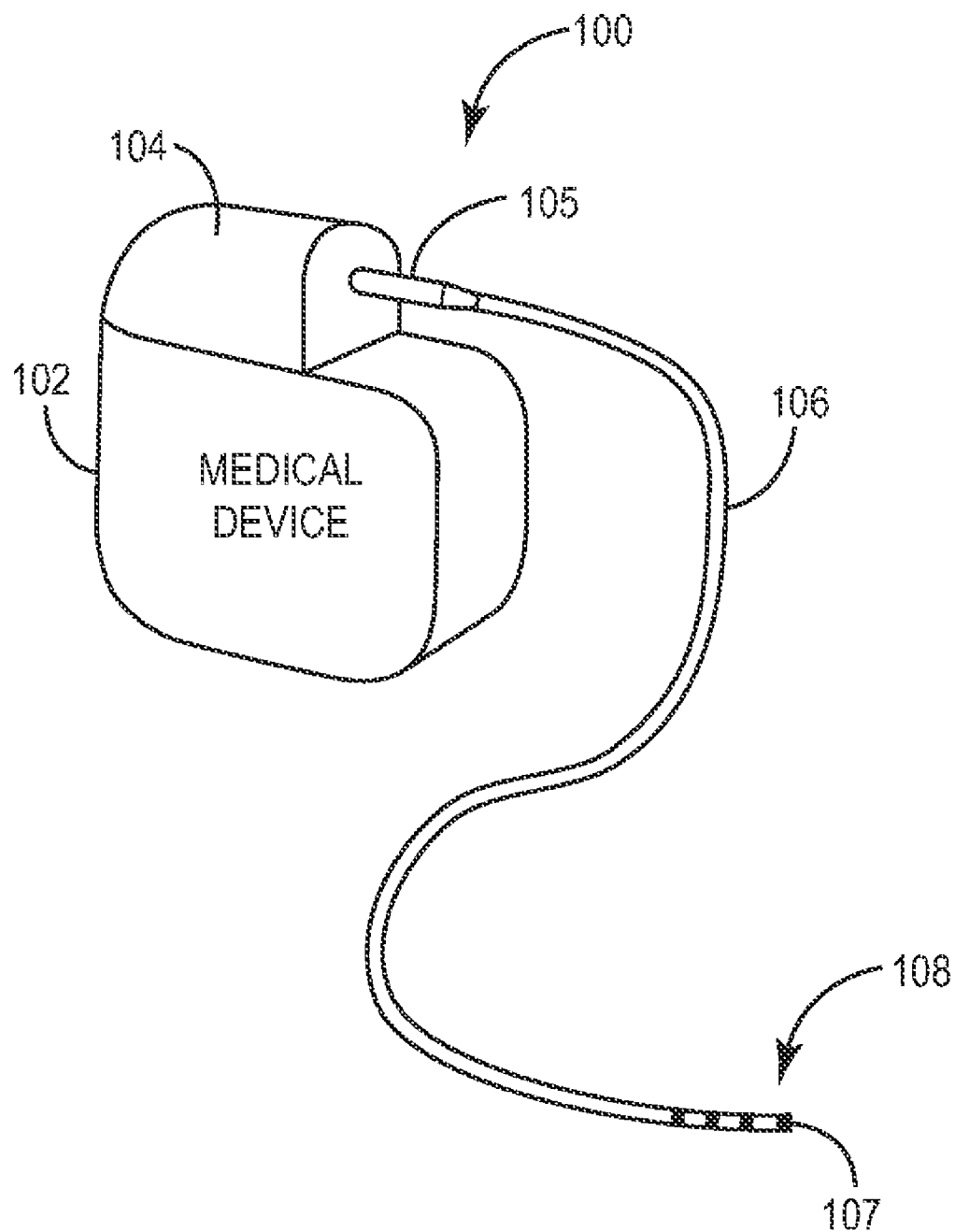
FIG. 1 is a block diagram of an implantable medical device.
Figure 2:
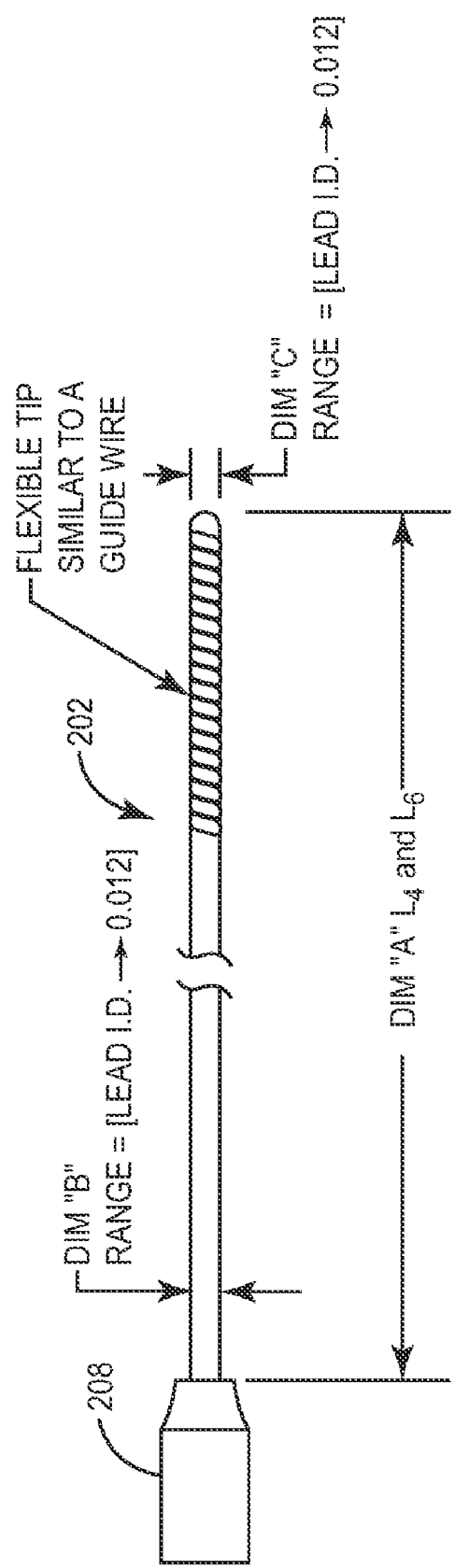
FIG. 2 is a plan view of a delivery device used in a medical lead.
Figure 3:
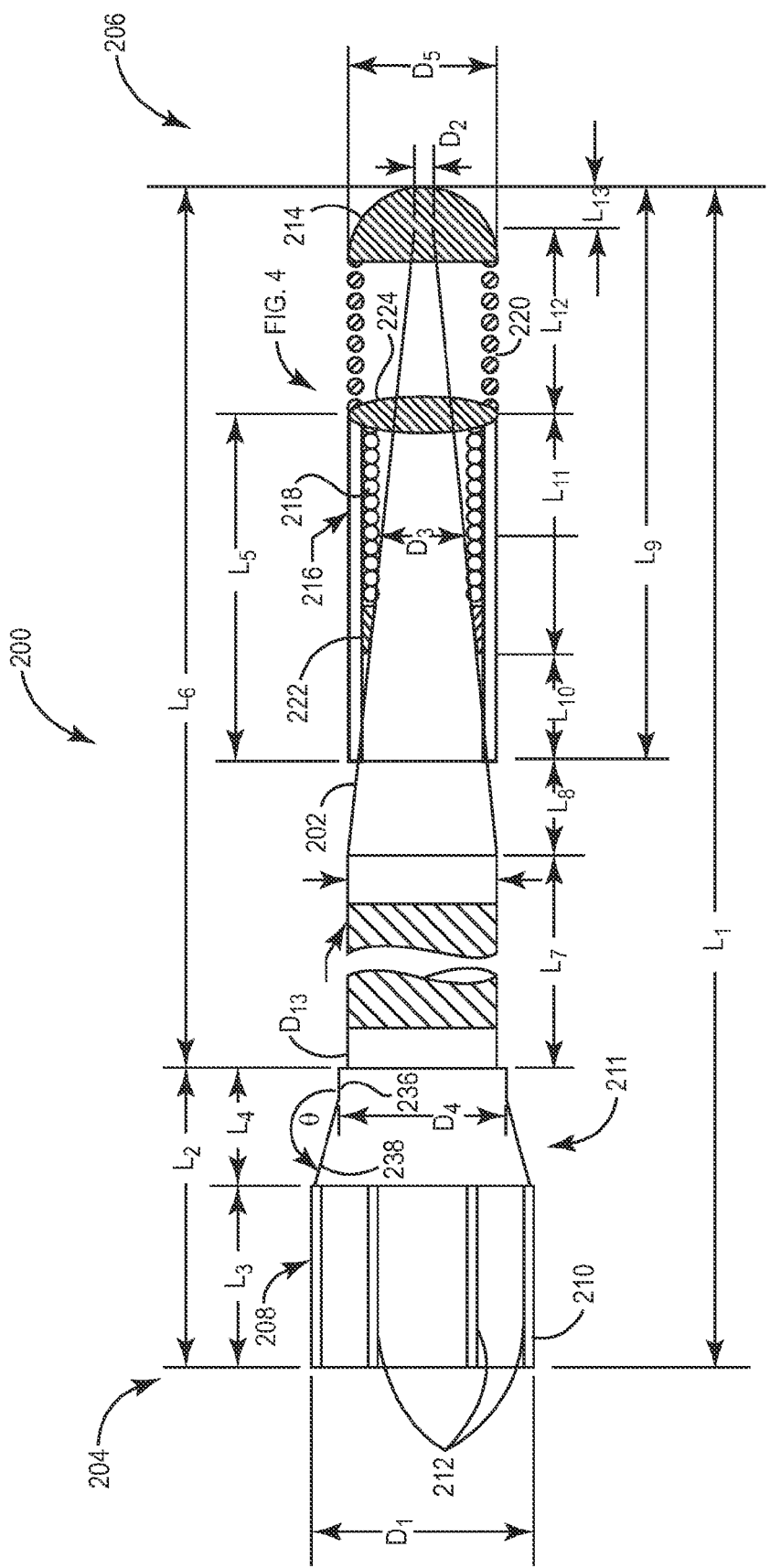
FIG. 3 is a cross-sectional view of a delivery device of FIG. 2.

The following description of embodiments is merely exemplary in nature and is in no way intended to limit the invention, its application, or uses. For purposes of clarity, the same reference numbers are used in the drawings to identify similar elements.

The present invention is directed to a delivery device that eases placement of a medical lead in the heart (e.g. coronary vein, left heart etc.) of a patient. Additionally, a lower manufacturing cost exists to produce the delivery device. For example, a single delivery device replaces both a guidewire and a stylet to place a lead in the left heart.

The delivery device is a hybrid of a guidewire and a stylet. The medical lead delivery device includes an elongated body, a controller, a first and second spring, and a sleeve. The elongated body includes a proximal end and a distal end. The controller is disposed at the proximal end and provides enhanced control of the distal tip of the elongated body. In particular, the delivery device can be advanced beyond the tip of the lead to provide a "rail" for the medical lead to track. The first and second springs are coupled to the distal end of the elongated body. A sleeve is coupled to the elongated body and to the first and second springs through first, second and third solder elements. The delivery device is able to place a lead in the small left ventricle vein(s) without using both a guidewire and a stylet.

FIG. 1 depicts a medical device system 100. A medical device system 100 includes a medical device housing 102 having a connector module 104 that electrically couples various internal electrical components of medical device housing 102 to a proximal end 105 of a medical lead 106. A medical device system 100 may comprise any of a wide variety of medical devices that include one or more medical lead(s) 106 and circuitry coupled to the medical lead(s) 106. An exemplary medical device system 100 may take the form of an implantable cardiac pacemaker, an implantable cardioverter, an implantable defibrillator, an implantable cardiac pacemaker-cardioverter-defibrillator (PCD), a neurostimulator, or a muscle stimulator. Medical device system 100 may deliver, for example, pacing, cardioversion or defibrillation pulses to a patient via electrodes 108 disposed on distal end 107 of one or more lead(s) 106. In other words, lead 106 may position one or more electrodes 108 with respect to various tissue (e.g. cardiac tissue etc.) locations so that medical device system 100 can deliver pulses to the appropriate locations.

Lead 106 is provided with an elongated insulative lead body (e.g. insulative polymeric tube etc.), which carries a coiled conductor therein. Other lead body types may be substituted within the context of the present invention, including lead bodies employing multiple lumen tubes and/or stranded or braided conductors as disclosed in U.S. Pat. No. 5,584,873 issued to Shoberg et al, and incorporated herein by reference in relevant part. Alternatively, the lead may include additional conductors arranged either within a multi-lumen lead body or concentrically, as disclosed in U.S. Pat. No. 4,355,646 issued to Kallok et al and incorporated herein by reference in relevant part. Additional pacing electrodes, sensors, or defibrillation electrodes, may of course be added to the lead body and coupled to additional conductors.

At the proximal end of the lead body is a connector assembly (e.g. industrial standard (IS)-1, IS-4 connector assemblies etc.) used in commercially available cardiac pacing leads. The connector assembly includes a conductive connector pin which is coupled by means of the conductor within the lead body to a tip electrode located at the distal tip of lead 106.

FIGS. 2-6 depict details of a delivery device 200 (or delivery wire) inserted into a lumen (not shown) of lead 106 in order to position lead 106 in a patient's body (e.g. left heart etc.). Delivery device 200 has a proximal end 204 and a distal end 206. Delivery device 200 comprises a controller 208, an elongated member 202, a sleeve 216, conductive springs (or coils) 218, 220 and solder coupled to springs 218, 220 and to sleeve 216. Elongated member 202 comprises a conductive material (e.g. stainless steel, NiTiNOL (i.e. a family of nickel (Ni)-titanium (Ti) alloys etc.)) with a length up to L1 and a diameter that ranges from D1 to D4. At proximal end 204 is controller 208. Controller 208 is an ergonomic member or knob configured to allow more control of the distal tip of elongated member 202 relative to lead 106. In particular, controller 208 assists in advancing delivery device 200 beyond the distal tip of lead 106 to provide a "rail" for the lead 106 to track. In one embodiment, controller 208 is permanently attached to elongated member 202. An exemplary permanent attachment includes an adhesive between controller 208 and elongated member 202. In another embodiment, controller 208 is temporarily coupled to elongated member 202 to allow controller 208 to be removed from elongated member 202. For example, controller 208 may be screwed onto the proximal end 204 of elongated member 202. Other suitable means may be used to connect controller 208 with proximal end 204. In another embodiment, controller 208 and elongated member 202 may be formed as a single part without any attachments therebetween.

In one embodiment, controller 208 comprises a gripping member 210 and a tapered distal end 211 with a length of about L2. Gripping member 210 is substantially cylindrically shaped and includes a diameter of about D1 and a length that extends L3. During insertion of a lead 106 into a patient, gripping member 210 is typically held between the thumb and the forefinger of the person attempting to place the lead 106 in the left heart. In one embodiment, gripping member 210 includes elongated recessed regions 212 to enhance the person's ability to hold gripping member 210. Other suitable ergonomic features (e.g. crossed recessed regions, rough textured outer surface etc.) may be used. At the distal end of gripping member 210 is a tapered distal end 211. Tapered distal end 211 includes a diameter D4, a length L4, and angle θ formed by first and second sides 236, 238. Angle θ ranges from about 120 degrees (°) to about 170°. Tapered distal end 211 of controller 208 is configured to receive the proximal end of elongated member 202. The proximal end of elongated member 202 includes a diameter D13.

Figure 4:
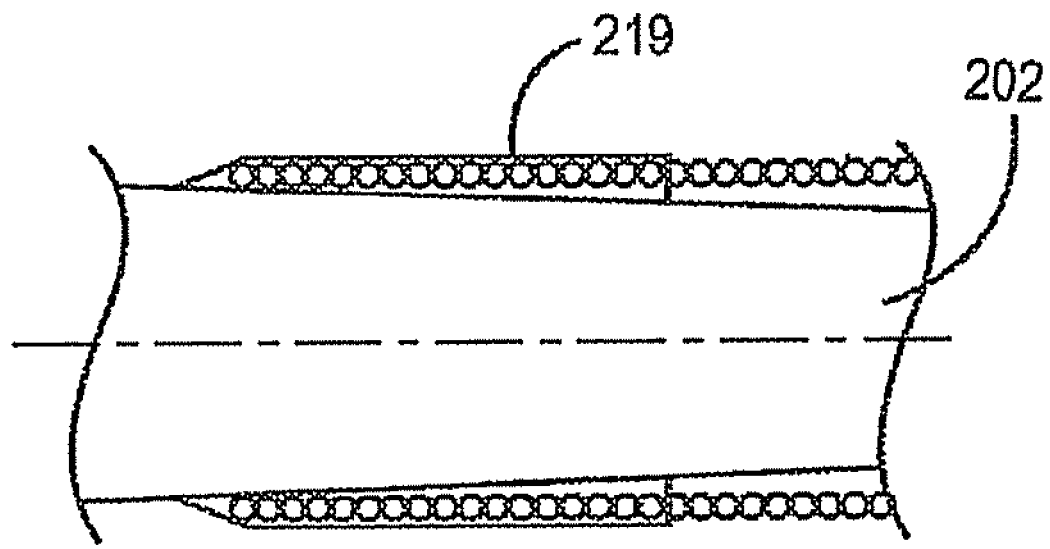
FIG. 4 is an enlarged view of a proximal joint of the delivery device depicted in FIG. 3.
Figure 5:
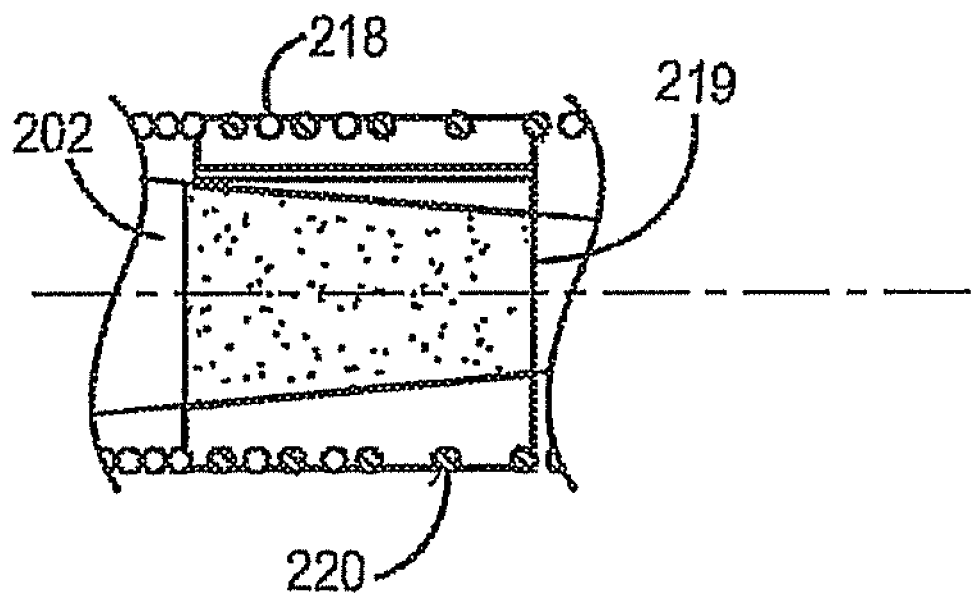
FIG. 5 is an enlarged view of a distal joint of the delivery device depicted in FIG. 3.
Figure 6:
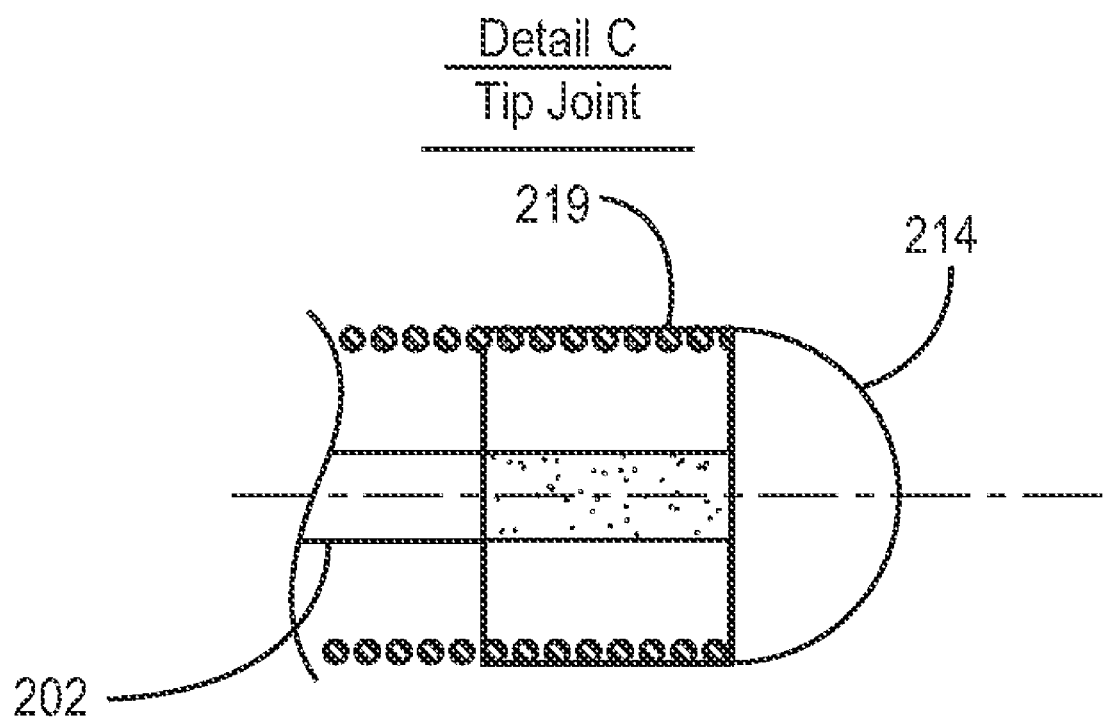
FIG. 6 is an enlarged view of a tip joint of the delivery device depicted in FIG. 3.

A distal portion of elongated member 202 is surrounded by cylindrical sleeve 216 with spring 218 disposed between an inner wall of sleeve 216 and elongated member 202. Sleeve 216 provides lubricity for moving within a lead body and also assists in coil alignment between springs 218, 220. The lubricous nature of sleeve 216 is due, at least in part, to being comprised of polyethylene terephthalate. Sleeve 216 extends a length of L5 and includes an inner diameter of $D_{sleeve}$. Solder 224 (also referred to as a second solder element) connects sleeve 216 to elongated member 202, and to springs 218, 220. Solder 224 is introduced over spring 218 and sleeve 216 at a high temperature. Referring briefly to FIGS. 4-6, the proximal joint, distal, tip joints, also include high temperature solder 219.

Elongated member 202 extends a length of L6, which is comprised of regions defined by lengths L7, L8, and L9. The L7 region includes a diameter D13 whereas the L8 region is tapered at its distal end and contacts sleeve 216. The L8 region has a diameter that ranges from about $D8_{small}$ to about $D8_{large}$. The L9 region is tapered and includes regions L10, L11, L12, and L13. The L10 region includes a tapered section of elongated member 202 defined by a diameter that ranges from about $D10_{small}$ to about $D10_{large}$. At the distal end of the L10 region is solder element 222 formed from high temperature solder. Solder element 222, also referred to as a third solder element, connects sleeve 216 with spring 218 and elongated member 202. Region L11 depicts spring 218 around elongated member 202. Region L11 includes a tapered section of elongated member 202 defined by a diameter that ranges from about $D11_{small}$ to about $D11_{large}$. The L12 region extends from solder elements 224 and 214. The distal tip of elongated member 202 extends into solder 214 which increases isodymetry and body (or stiffness) to elongated member 202. As shown, the distal tip of elongated member 202 does not extend beyond solder 214 (also referred to as the first solder element). Solder 214 has a diameter of about D5. Solder 214, comprising a low temperature solder, is placed over the tip of the coil and to the distal tip of elongated member 202.

Springs 218, 220 are formed from any desired conductive material, selected based on the application of the elongated member being manufactured. Conductive material includes conductive metals or alloys, and/or conductive polymers. For example, springs 218, 220 may be formed from silver, platinum, gold, copper, a conductive alloy, or any other conductive material suitable for use in a medical lead 106.

Provided in Table 1 are the general dimensions for a delivery device 200 made to deliver 4 and 6 French leads.

TABLE 1

Dimensions of a delivery device.

| Element designation | Dimension of a 4 French delivery device | Dimension of a 6 French delivery device |
|---|---|---|
| L1 | 43.01 inches | 43.01 inches |
| L2 | 0.49 inches | 0.49 inches |
| L3 | 0.395 inches | 0.395 inches |
| L4 | 0.093 inches | 0.093 inches |
| L5 | 8.66 inches | 8.66 inches |
| L6 | 42.52 inches | 42.52 inches |
| L7 | 28.7 inches | 29.1 inches |
| L8 | 3.15 inches | 2.76 inches |
| L9 | 11.02 inches | 11.02 inches |
| L10 | 5.12 inches | 5.91 inches |
| L11 | 3.54 inches | 2.76 inches |
| L12 | 2.36 inches | 2.36 inches |
| L13 | 0.08 inches | 0.08 inches |
| D1 | 0.19 inches | 0.19 inches |
| D2 | 0.0024 inches | 0.0024 inches |
| D3 | 0.009 inches | 0.012 inches |
| D4 | 0.125 inches | 0.125 inches |
| D5 | 0.012 inches | 0.012 inches |
| D13 | 0.014 inches | 0.014 inches |

Another embodiment of length of L1 is about 34 inches. Yet another embodiment of length of L1 is about 51 inches. L1 can range from about 34 inches to about 51 inches with the remaining lengths being adjusted (i.e. increased or decreased) to accommodate the lengths of L1. In another embodiment, L1 is greater than 51 inches.

The discussion now turns to conventional guidewires that merely move inside a lumen without passing electrical signals therethrough to a programmer (not shown) to map potential placement sites of a lead. More specifically, conventional guidewires are placed in a certain position by an implanting physician and then pacing may be performed. The location of the conventional lead may not be the optimal location, which compels the physician to continue to seek the proper location of the lead.

Figure 7A:
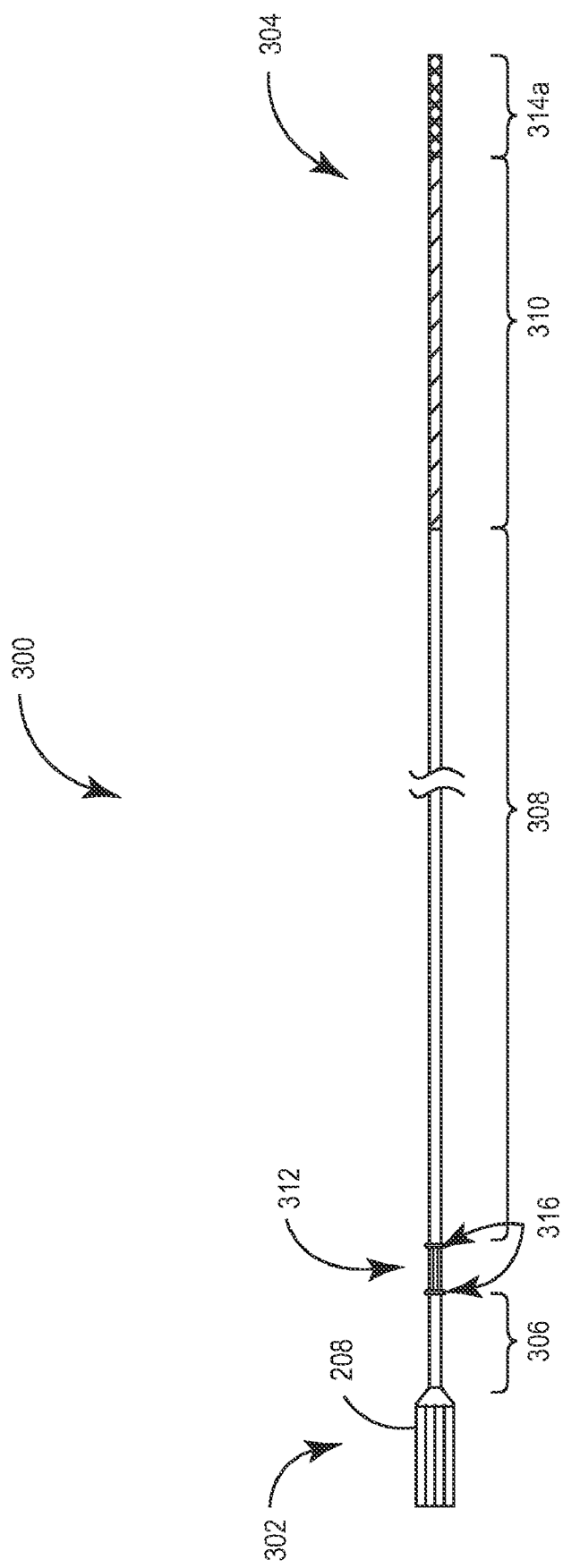
FIG. 7A is a plan view of a mapping guidelet that electronically maps potential sites to position the lead.
Figure 7B:
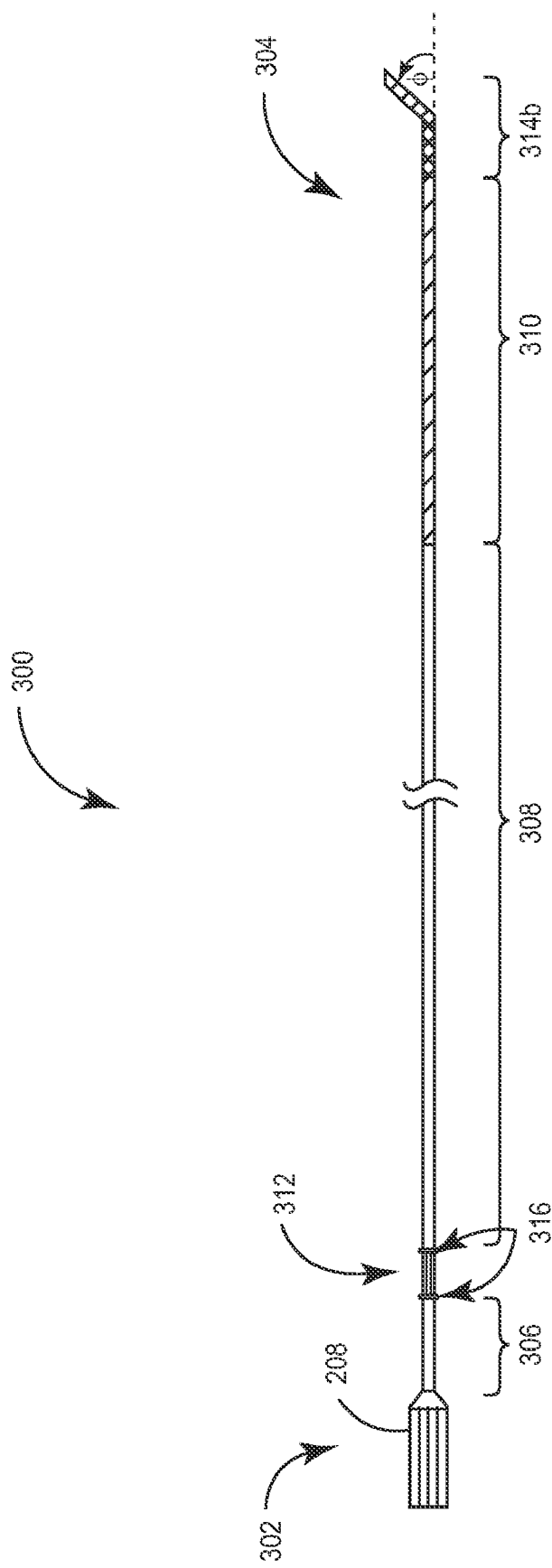
FIG. 7B is a plan view of another embodiment of a mapping guidelet configured to map potential sites to position the lead.
Figure 7C:
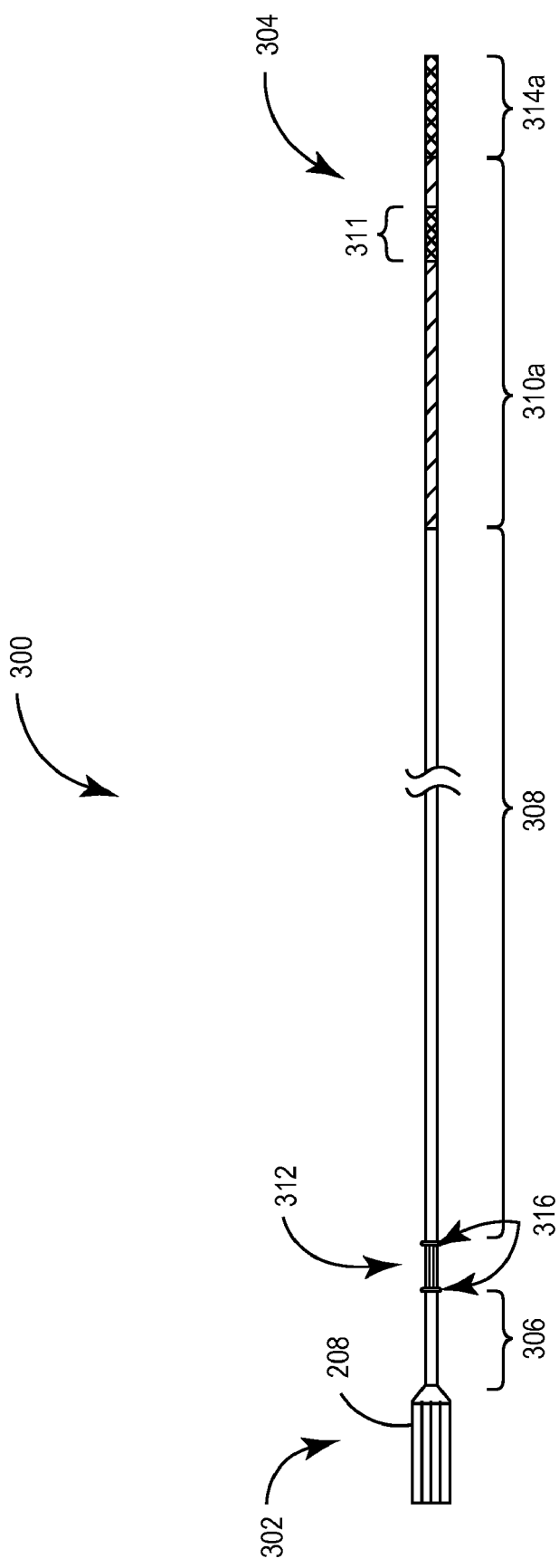
FIG. 7C is a plan view of another embodiment of a mapping guidelet configured to map potential sites to position the lead through bi-polar sensing.

Another embodiment of the claimed invention relates to a mapping guidelet 300 (also referred to as a mapping hybrid stylet/guidewire), depicted in FIGS. 7A-7C. Mapping guidelet 300 aids in delivery of lead 106 by simultaneously guiding and electrically mapping potential sites for placement of lead 106 into a vein or artery of a patient. In particular, an implanting physician is able quickly subselect the various vein locations/pacing sites through measured electrical values for desired pacing locations prior to placing the left heart lead. Consequently, mapping guidelet 300 reduces time spent and discomfort to the patient in properly locating lead 106 in the patient's vein or artery.

Mapping guidelet 300 includes proximal and distal ends 302, 304, respectively. Additionally, mapping guidelet 300 further comprises an electrically active distal segment 314a, b, an uncoated conductive segment 312, a first, second, and third coated segments 306, 308, 310, respectively. Referring briefly, to FIGS. 7A-7B, active distal segment 314a,b may be a straight distal tip 314a or a curved distal tip 314b that is electrically active with a surface area of about 3 to 7 square millimeters. Curved distal tip 314b possesses an angle φ that ranges from about 45 degrees (°) to about 60°. In one embodiment, the electrically active wire surface area of distal segment 314a, b, is treated with an enhanced sensing surface such as titanium nitride (TiN) or a platinum black oxide. Treating the electrically active wire surface area of distal segment 314a,b with TiN or a platinum black oxide improves the ability to sense R-waves in the coronary vein locations.

Each coated segment 306, 308, 310 may have a coat thickness that ranges from about 0.0002 inches to about 0.002 inches. The coat thickness is created by applying multiple coats over elongated member 202. First, second, and third coated segments 306, 308, 310, may be coated with a variety of materials. Exemplary coating materials include hydrolytically stable polyimide (e.g. soluble imide (SI) polyimide material (formerly known as Genymer, Genymer Si, and LARC SI), polytetrafluorethylene (PTFE), parlyene (e.g. parlyene C), or other suitable materials. Si polyimide is typically stiffer than PTFE and parylene. In contrast to hydrolytically stable polyimide and PTFE, parylene is vacuum deposited; therefore parylene generally forms very thin thicknesses (e.g. <0.0002 inches, or sometimes microns to Angstroms thick etc.).

In one embodiment, second coated segment 308 consists essentially of parlyene and third coated segment consists essentially of PTFE. In another embodiment, first, second, and third coated segments 306, 308, 310, are each coated with different materials. In yet another embodiment, first, second, and third coated segments 306, 308, 310, are each coated with the same materials.

Uncoated conductive segment 312 (bare wire etc.) is located at proximal end 302. Essentially, uncoated conductive segment 312 is a portion of elongated member 202 without any material being disposed thereon. Retaining rings 316 are disposed at the proximal and distal ends of conductive element 312. Retaining rings 316 serve the purpose of keeping a programmer clip (i.e. cable connection) (not shown) within the conductive area of conductive segment 312. U.S. Pat. No. 6,325,756 issued to Webb et al, incorporated herein by reference in relevant part, discusses programmers in greater detail. Retaining rings 316 hold the programmer clip (not shown) when electrical thresholds are sampled via a programmer cable, measuring R-waves from the exposed distal tip 314a,b. The implanting physician may leave the programmer clip attached and continuously or periodically sample the voltage at the distal tip of elongated member 202 as it is passed and placed in the coronary veins.

In one embodiment, the sampled electrical data relates to voltage levels obtained the exposed distal tip 314a,b. The amplitude from a sampled voltage level is compared to the amplitude of a reference voltage level. In one embodiment, mapping guidelet 300 is unipolar in its sensing ability since a reference voltage level is obtained from uncoated segment 310. In another embodiment, mapping guidelet 300 is bipolar in its sensing ability since an amplitude of the reference voltage level is obtained from a conductive ring 311, shown in FIG. 7C, and compared to the amplitude of the actual voltage from active distal tip 314 a,b. Conductive ring 311 is electrically active and includes a positive clip zone for receiving the pacing clip from the programmer.

Figure 8A:
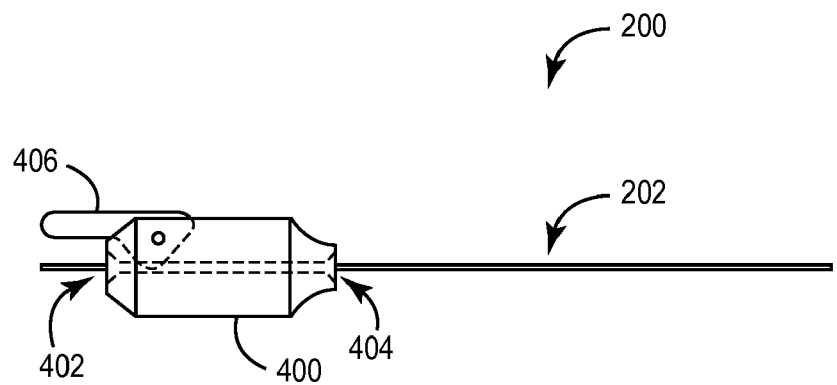
FIG. 8A depicts a plan view of a delivery device controller in an unlocked position.
Figure 8B:
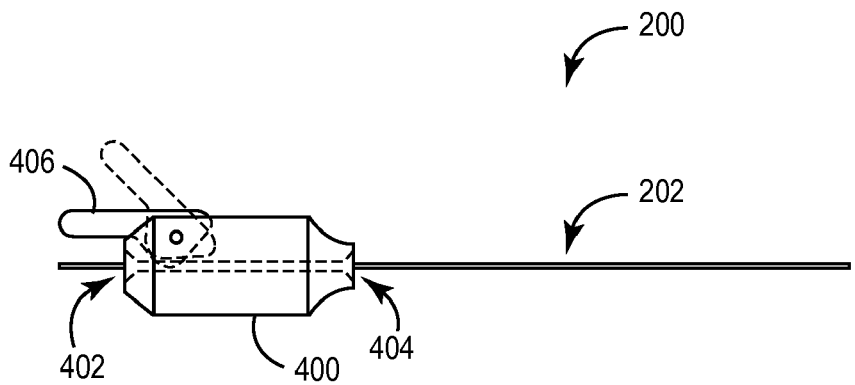
FIG. 8B depicts a plan view of a delivery device controller in a locked position.
Figure 9:
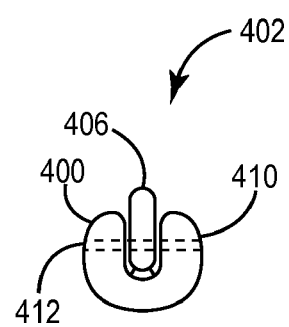
FIG. 9 depicts a plan view of a proximal end of a delivery device controller.

Another embodiment of the claimed invention relates to controller 400 of a delivery device 200 depicted in FIGS. 8A-8B, and 9. Controller 400 is slideably adjustable along the length of a proximal end of lead 106. Controller 400 has a proximal and distal ends 402, 404 respectively and comprises a lever 406, a body 410 and a pin 412. Lever 406 is used to engage and disengage controller 400 from elongated body of lead 106. Body 410 has a locking interference fit to clamp onto about a 0.01 inch to 0.016 inch outer diameter of elongated member 202. The interference fit should allow up to 0.005 inches. More particularly, an interference range should be 0.0003 to about 0.0005 inches. The interference fit between body 410 and elongated member 202 occurs when lever 406 is engaged (FIG. 8B), thereby clamping onto elongated member 202.

Various embodiments of the invention have been described. There are a variety of additional embodiments related to delivery device 200 that are within the scope of the claimed invention. For example, elongated member 202 (also referred to as the central core wire) may have various dimensional combinations to alter the stiffness of the delivery device 200 along its length. Elongated member 202 could also be comprised of differing raw materials depending on the specific clinical application of the wire. In addition, the distal and proximal coils that cover the core wires may be replaced with a polymeric sleeve material of various inner and outer diameters, in fact in some embodiments the entire length of the core wire might be covered with a polymeric sleeve material. These sleeve materials could be of differing raw materials depending on whether the sleeve will perform the function of acting as the wire tip, or shaft segment. The outer coating utilized on the wire could be of a hydrophilic or hydrophobic nature depending on the specific clinical application.

Another embodiment involves a slideable torque tool may be employed. This embodiment is implemented through side loading and/or a torque-limiting (or a slip clutch mechanism) that engage with the lead via a connector. In another embodiment, for ease of torquing delivery device 200, a proximal end is configured with square (or a non-rounded) cross-section, segmented round to non-round. In yet another embodiment, the delivery device is configured with alternating floppy and stiff areas. In still yet another embodiment, a coupling and decoupling via a lead and wire mechanism is disclosed. In yet another embodiment, an infusion wire with an injection lumen and sideport are used to inject contrast through the lumen. In yet another embodiment, a mechanism is employed for using a temperature sensitive alloy for lead fixation. In yet another embodiment, a pacing wire may include unipolar and/or bi-polar configuration. This may include a cathode range: 1.5 mm$^2$ to 15 mm$^2$-5 mm$^2$ nominal and/or an anode range: 5 mm$^2$ to 30 mm$^2$-10 mm$^2$ nominal. In yet another embodiment, a telescoping delivery device is employed. In yet another embodiment, the delivery device includes a centering/loading tool.

While the invention has been described in its presently preferred form, it will be understood that the invention is capable of modification without departing from the spirit of the invention as set forth in the appended claims.

The invention claimed is:

1. A medical lead delivery device comprising:
   an elongated body extending from a proximal end to a distal end, wherein the elongated body comprises a conductive material, and further wherein the elongated body further comprises a tapered section at the distal end of the elongated body;
   a controller disposed on the elongated body;
   a first coil extending from a proximal end to a distal end and surrounding at least a portion of the tapered section of the elongated body, wherein the distal end of the first coil is located closer to the distal end of the elongated body than the proximal end of the first coil, wherein the first coil comprises conductive material, and further wherein the proximal end of the first coil is electrically coupled to the tapered section of the elongated body;
   a second coil extending from a proximal end to a distal end and surrounding at least a portion of the tapered section of the elongated body, wherein the proximal end of the second coil is electrically coupled to the distal end of the first coil, wherein the distal end of the second coil is located closer to the distal end of the elongated body than the proximal end of the second coil, and further wherein at least a portion of the second coil is uninsulated so as to be operable for use in measuring electrical values of body tissue; and
   insulative material surrounding at least the first coil such that the first coil is disposed between the insulative material and the elongated body and wherein the diameter of the first coil is less than the diameter of the second coil.

2. The medical lead delivery device of claim 1, wherein the medical lead delivery device further comprises a solder element electrically coupling the distal end of the elongated body to the distal end of the second coil forming a distal tip of the medical lead delivery device, and further wherein the distal tip extends distally from the distal end of the elongated body and the distal end of the second coil.

3. The medical lead delivery device of claim 1, wherein the medical lead delivery device further comprises a solder element electrically coupling the tapered section of the elongated body, the distal end of the first coil, and the proximal end of the second coil.

4. The medical lead delivery device of claim 1, wherein the medical lead delivery device further comprises a solder element electrically coupling the tapered section of the elongated body to the proximal end of the first coil.

5. The medical lead delivery device of claim 1, wherein the elongated body ranges in length from about 34 inches to about 51 inches.

6. The medical lead delivery device of claim 1, wherein the elongated body is about 34 inches.

7. The medical lead delivery device of claim 1, wherein the medical lead delivery device is a hybrid of a stylet and a guidewire.

8. The medical lead delivery device of claim 1, wherein the medical lead delivery device is a unitary element.

9. The medical lead delivery device of claim 1, wherein the medical lead delivery device is not a separate guidewire and a separate stylet.

10. The medical lead delivery device of claim 1, wherein the medical lead delivery device is adapted to insert a medical lead into a right atrium through to a coronary vein without using a stylet and a guidewire.

11. The medical lead delivery device of claim 1, wherein the controller is slideably adjustable along at least a portion of a length of the medical lead delivery device.

12. The medical lead delivery device of claim 1, wherein the insulative material comprises a sleeve.

13. The medical lead delivery device of claim 1, wherein the insulative material comprises a coating.

14. The medical lead delivery device of claim 1, wherein the diameter of the elongated body is about 0.014 inches or less.

15. The medical lead delivery device of claim 1, wherein the diameter of the first coil is smaller than the diameter of the second coil.

16. The medical lead delivery device of claim 1, wherein the medical lead delivery device further comprises a distal tip extending distally from the distal end of the second coil and the distal end of the elongated body, wherein the at least a portion of the second coil that is uninsulated is adjacent the distal tip, and further wherein the length of the at least a portion of the second coil that is uninsulated is greater than the length of the distal tip.

17. A medical lead delivery device comprising:
   an elongated body extending from a proximal end to a distal end, wherein the elongated body comprises a conductive material, and wherein the elongated body further comprises a tapered section at the distal end of the elongated body;
   a first coil extending from a proximal end to a distal end and surrounding at least a portion of the tapered section of the elongated body, wherein the distal end of the first coil is located closer to the distal end of the elongated body than the proximal end of the first coil, wherein the first coil comprises conductive material, and further wherein the proximal end of the first coil is electrically coupled to the tapered section of the elongated body;
   a second coil extending from a proximal end to a distal end and surrounding at least a portion of the tapered section of the elongated body, wherein the distal end of the second coil is located closer to the distal end of the elongated body than the proximal end of the second coil, wherein the second coil comprises conductive material, wherein the proximal end of the second coil is electrically coupled to the distal end of the first coil, wherein at least a portion of the second coil is uninsulated so as to be operable for use in measuring electrical values of body tissue; and
   insulative material surrounding at least the first coil, wherein the insulative material further surrounds the elongated body between the proximal end of the first coil and the proximal end of the elongated body such that at least a portion of the elongated body near the proximal end of the elongated body is configured for sampling electrical values therefrom and wherein the diameter of the first coil is less than the diameter of the second coil.

18. The medical lead delivery device of claim 17, wherein the medical lead delivery device further comprises a solder element electrically coupling the distal end of the elongated body to the distal end of the second coil forming a distal tip of the medical delivery device, and further wherein the distal tip extends distally from the distal end of the elongated body and the distal end of the second coil.

19. A medical lead delivery device of claim 18, wherein the distal tip is about 2-6 sq. mm.

20. The medical lead delivery device of claim 17, wherein the medical lead delivery device further comprises a solder element electrically coupling the tapered section of the elongated body, the distal end of the first coil, and the proximal end of the second coil.

21. The medical lead delivery device of claim 17, wherein the medical lead delivery device further comprises a solder element electrically coupling the tapered section of the elongated body to the proximal end of the first coil.

22. The medical lead delivery device of claim 17, wherein the insulative material comprises a sleeve.

23. The medical lead delivery device of claim 17, wherein the insulative material comprises a coating.

24. The medical lead delivery device of claim 17, wherein the diameter of the elongated body is about 0.014 inches or less.

25. The medical lead delivery device of claim 17, wherein the diameter of the first coil is smaller than the diameter of the second coil.

26. The medical lead delivery device of claim 17, wherein the medical lead delivery device further comprises a distal tip extending distally from the distal end of the second coil and the distal end of the elongated body, wherein the at least a portion of the second coil that is uninsulated is adjacent the distal tip, and further wherein the length of the at least a portion of the second coil that is uninsulated is greater than the length of the distal tip.

* * * * *